United States Patent [19]

Ching

[11] 4,263,222
[45] Apr. 21, 1981

[54] DICHLOROFORMATES

[75] Inventor: Ta-Yen Ching, Schenectady, N.Y.

[73] Assignee: General Electric Company, Schenectady, N.Y.

[21] Appl. No.: 123,668

[22] Filed: Feb. 22, 1980

[51] Int. Cl.$^3$ .................................. C07C 69/96
[52] U.S. Cl. ........................... 260/463; 528/192; 528/204
[58] Field of Search ......................................... 260/463

[56] References Cited

FOREIGN PATENT DOCUMENTS 335235  5/1972  U.S.S.R. ............................... 260/463

Primary Examiner—Donald G. Daus
Assistant Examiner—M. C. Eakin
Attorney, Agent, or Firm—Joseph T. Cohen; James C. Davis, Jr.

[57] ABSTRACT

Certain dichloroformates are described which have utility for imparting UV stability to polycarbonate resins which are interpolymerized with the former.

5 Claims, No Drawings

DICHLOROFORMATES

This invention is concerned with novel compositions of matter comprising a certain class of dichloroformates (hereinafter so identified). More particularly, the invention is concerned with compositions of matter having the general formula

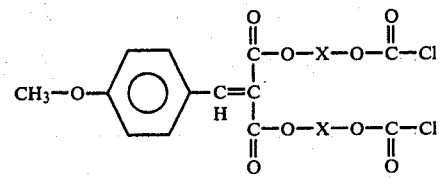

where X is a divalent saturated $C_2$-$C_{10}$ alkylene group. Among the divalent saturated alkylene groups X can represent are, for instance,
—$CH_2CH_2$—, —$CH_2$—$(CH_2)_2$—$CH_2$—, —$CH_2$—$(CH_2)_4$—$CH_2$—, —$CH_2$—$C(CH_3)_2$—$CH_2$—, —$CH_2$—$(CH_2)_8$—$CH_2$—, etc.

These compositions of formula I can be interpolymerized with many aromatic dihydric compounds to make polycarbonate resins which have a built in UV stability as contrasted to the same polycarbonate resins which are free of such interpolymerized stabilizing units. The use of dichloroformates of formula I interpolymerizes with dihydric aromatic compounds for imparting UV stability to polycarbonate resins is more particularly disclosed and claimed in my copending application Ser. No. 123,667 filed concurrently herewith and assigned to the same assignee as the present invention. By reference, this latter application is incorporated in the disclosures and teachings of the instant application.

The dichloroformates of the present invention may be obtained by first effecting formation of p-methoxybenzylidene dimethyl malonate having the formula

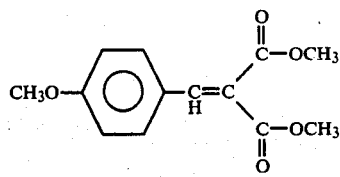

The compound of formula II can be made from p-methoxybenzaldehyde and dimethyl malonate. p-methoxybenzylidene dimethyl malonate is a commercial UV stabilizer known as Cyasorb 1988 manufactured by American Cyanamide. The p-methoxybenzylidene dimethyl malonate of formula II is then interacted with a glycol of the formula

III. HO—X—OH in the presence of sodium methoxide to give a compound of the formula

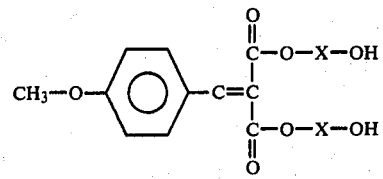

where X has the meanings given above. Thereafter, the compound of formula IV is treated in accordance with my invention with phosgene to form the compound of formula I.

In order that those skilled in the art may better understand how the present invention may be practiced, the following examples are given by way of illustration and not by way of limitation. All parts are by weight unless otherwise indicated.

EXAMPLE 1

This example illustrates the preparation of the compound corresponding to the formula

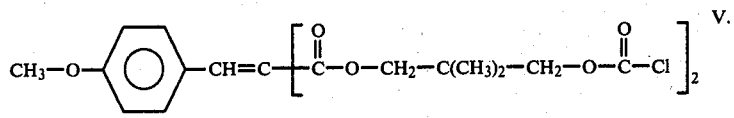

More particularly, 191 grams (1.45 mols) dimethyl malonate, 198 grams (1.45 mols) para-methoxybenzaldehyde, 30 grams ammonium acetate, 85 grams acetic acid, and 500 ml benzene were heated at the reflux temperature of the mass with a Dean Stark trap until 1.45 mols of water had been removed. The solution was cooled, washed with water, and dried. The volatile unreacted starting materials were removed by vacuum distillation and the residue recrystallized from methanol to give the compound having the formula

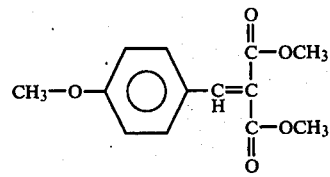

The identity of this compound (known as Cyasorb 1988) was established by NMR and had a melting point of 58°-60° C.

320 grams (3.0 mols) neopentyl glycol was added to 500 ml of a toluene solution containing 350 grams (1.4 mols) of the compound of formula V together with 0.2 grams sodium methoxide. The ester exchange reaction was driven to completion by distilling off the methanol which was formed. The solution was washed with 5% HCl, 5% sodium bicarbonate, and water, dried and recrystallized from toluene to give a product having the formula

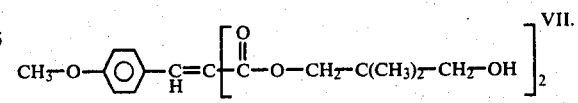

in a yield of 93% and melting at 111°–113° C. The identity of this compound was established by NMR and by ultraviolet analyses.

A three fold molar excess of phosgene was dissolved in a cold methylene chloride solution. One part of the compound of formula VII was introduced slowly into the phosgene solution and then warmed to room temperature (about 27° C.) while stirring the mixture. Excess phosgene was driven-off by purging the solution with nitrogen. The resulting bischloroformate obtained in the form of a methylene chloride solution had the formula

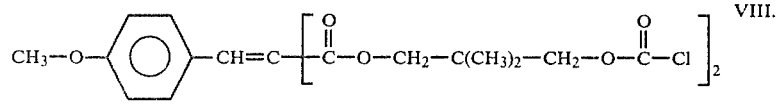 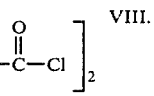  VIII.

EXAMPLE 2

Other dichloroformates of the general formula I can be obtained similarly as was done in Example 1 with the exception that instead of using neopentyl glycol, one would instead employ an equivalent amount of other glycols, such as ethylene glycol, butanediol, hexanediol, etc., to form compounds which respectively have the formulas.

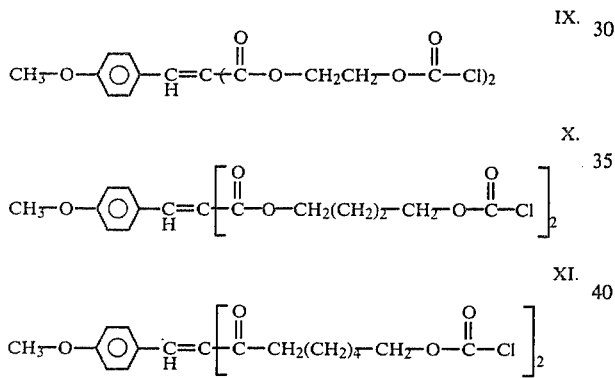

It will of course be apparent to those skilled in the art that in addition to the glycols used above, other glycols, many examples of which have been given previously may be employed to make other dichloroformates. The conditions of reaction can be modified considerably without in any way departing from the scope of the invention. The conditions recited in Example 1 generally are applicable to the making of any dichloroformate coming within the scope of formula I.

The bichloroformates of formula I can be intercondensed with dihydric phenols, such as Bisphenol-A in amounts ranging from about 0.1 to 25 mol percent or more based on the total molar concentration of the dichloroformate and the Bisphenol-A employed. The usual methods for making polycarbonate resins are more particularly described in U.S. Pat. Nos. 2,999,846, 2,946,766, and 2,950,266—Goldblum issued Aug. 23, 1960, and assigned to the same assignee as the present invention. It will be found that such resins having intercondensed residues from the dichloroformate of formula I have improved UV stability over the usual polycarbonate resins from which the residue of formula I is absent, or over polycarbonate resins which are commercially available and have mechanically incorporated therein known UV stabilizers. Such a comparison has been disclosed in my copending application Ser. No. 123,667 filed concurrently herewith and assigned to the same assignee as the present invention. By reference this latter application is made part of the disclosures and teachings of the instant application.

Polycarbonate resins, so stabilized have been used as glazing (window) materials, sheet materials, molded products, etc. in which resistance to UV light is an important consideration in determination of the particular application involved. These polycarbonate resins containing the residue from the dichloroformate of formula I and interpolymerized in the manner described above, can be used in window applications where UV stability is an important consideration, as packaging material, in the form of thin films, etc.

What I claim as new and desire to secure by Letters Patent of the United States is:

1. A dichloroformate of the general formula

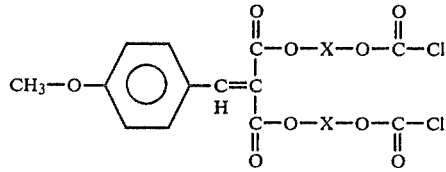

where X is independently a divalent saturated $C_2$–$C_{10}$ alkylene group.

2. A composition of matter having the formula

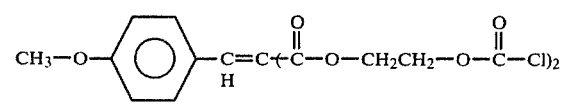

3. A composition of matter having the formula

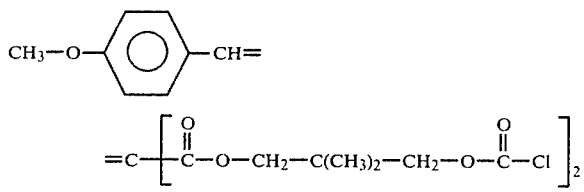

4. A composition of matter having the formula

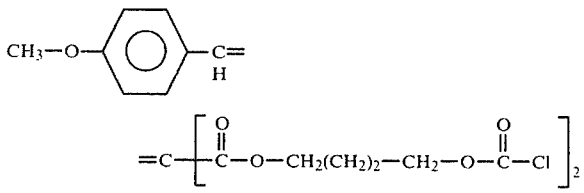

5. A composition of matter having the formula

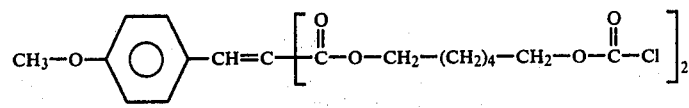

UNITED STATES PATENT AND TRADEMARK OFFICE
CERTIFICATE OF CORRECTION

PATENT NO. : 4,263,222
DATED : April 21, 1981
INVENTOR(S) : Ta-Yen Ching

It is certified that error appears in the above—identified patent and that said Letters Patent is hereby corrected as shown below:

Claim 3, the formula should read as follows:

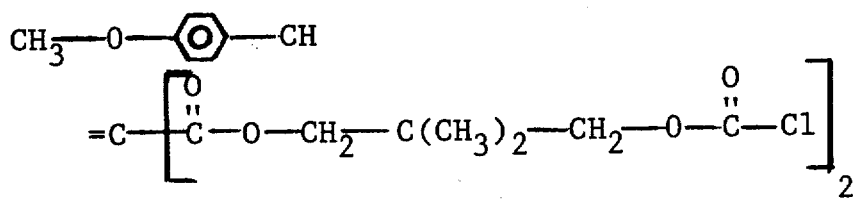

Claim 4, the formula should read as follows:

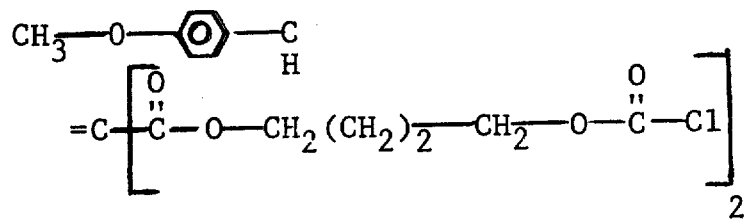

Signed and Sealed this

Twenty-eighth Day of July 1981

[SEAL]

Attest:

GERALD J. MOSSINGHOFF

Attesting Officer    Commissioner of Patents and Trademarks